July 24, 1973 S. R. SMITH Plant Pat. 3,376
AZALEA PLANT
Filed Jan. 24, 1972
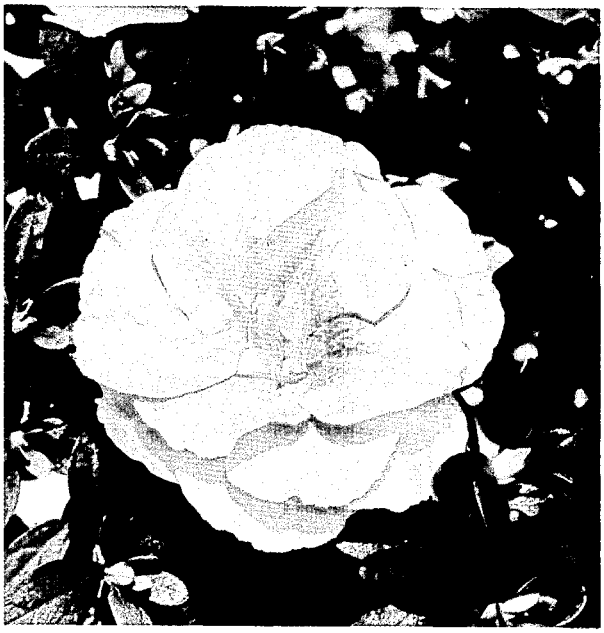
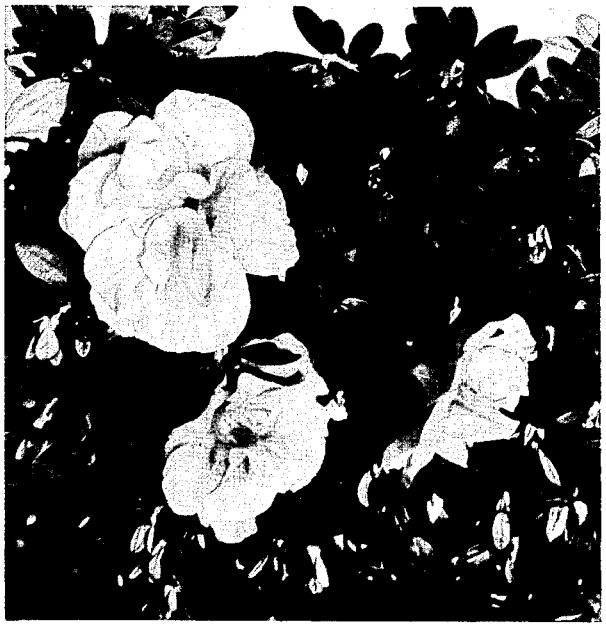

United States Patent Office

Plant Pat. 3,376
Patented July 24, 1973

3,376
AZALEA PLANT

Spencer R. Smith, Rockwood, Mich., assignor to Post Gardens, Inc., Rockwood, Mich.

Filed Jan. 24, 1972, Ser. No. 220,502
Int. Cl. A01h 5/00
U.S. Cl. Plt.—56 1 Claim The present invention comprises a new and distinct variety of azalea plant which is a sport of the commercial but unpatented variety known as Chimes.

The new variety was discovered in a greenhouse at Rockwood,Mich., from a block of flowering plants of the parent variety Chimes, and when asexually reproduced by stem and tip cuttings at Rockwood, Mich., has been found to retain its distinctive characteristics through successive propagations.

The reddish rose flower color of the new variety is generally similar to the flower color of the new variety is generally similar to the flower color of Chimes, but the new variety is distinguished from the parent Chimes by the following characteristics:

1. Profuse branching and rapid growth.
2. Earliness and reliable ease of forcing, with a minimum of dormancy, and without requiring artificial precooling.
3. A flower which is more flat in shape than the bell shaped flower of the parent.
4. More profuse flower production.
5. Slightly smaller but more abundant foliage, thereby giving a dense foliage arrangement.
6. Buds which set rapidly from even late pinching, and which mature rapidly.

Certain of the above distinguishing characteristics also apply as well to other commercial azalea varieties, for example, its profuse flowering and the ease and reliability of the new variety in being forced into early bloom without requiring precooling. To applicant's best knowledge the new variety is the only early season variety which can be grown for the Christmas market without requiring artificial precooling. This characteristics is of course highly significant from a commercial standpoint.

The accompanying photographic drawing illustrates the new variety, with the colors being as nearly true as possible with color photographs of this type.

The following is a detailed description of the new variety.

*Bontanical classification*: Rhododendron hybrida *evergreen type*

Flower:

*Color (greenhouse color in Rockwood, Mich.)*.—Deep reddish rose, with a few darker red spots in throat.

*Bud*.—Size—medium, opening habit—normal, quantity—profuse.

*Bloom*.—Size—approximately 2½"–3" in diameter; form—hose in hose, generally round and flat, with slightly serrated edges, compared with generally bell-shaped flower of parent; habit—profuse budding results in plant being essentially totally covered with blooms; response—early; life—normal, both in greenhouse and home.

*Blooming habit*.—Once, profusely; early season, normally in bloom for Christmas without requiring artificial precooling; minimum dormancy.

*Petals*.—Form—generally flat in shape; number—approximately 10, 5 main petals and 5 sub-stigma petals; color—generally deep reddish rose, with darker red spots in center of flower.

Reproductive organis:

*Stamens*.—From none to five, which change to small petals, in center of florescence.

*Filament*.—Generally reddish pink.

*Anthers*.—Generally red on bottom, yellow gray on top.

Foliage:

*Type*.—Evergreen.

*Shape*.—Elongated, oval, more rounded on the end of the leaf than pointed.

*Color*.—Dark greeen, glossy on top, light green underneath.

*Size*.—Relatively small.

*Quantity*.—Profuse, providing dense appearance of plant as a whole.

Plant: Bush.

*Growth habit*.—Profuse branching; strong and rapid growth, sets buds rapidly even from late pinching.

*Breaking habit*.—Forces easily into early bloom.

*Budding ease*.—Good.

*Size*.—Approximately 12" high and 12" in diameter at 8 months.

I claim:

1. A new and distinct variety of azalea plant characterized particularly as to uniqueness when compared to the parent variety Chimes by its profuse branching and rapid growth; earliness and reliable ease of forcing, with a minimum of dormancy, and without requiring artificial precooling; by its flowers, which are profuse and which are more flat in shape than the bell shaped flower of the parent variety; slightly smaller but more abundant foliage, and by its buds which set and mature rapidly, from even late pinching; the variety being uniquely characterized from all known azalea varieties by the ease and reliability of being forced into early bloom for the Christmas market without requiring artificial precooling.

No references cited.

ROBERT E. BAGWILL, Primary Examiner